United States Patent
Yang et al.

(10) Patent No.: US 6,610,035 B2
(45) Date of Patent: *Aug. 26, 2003

(54) HYDROPHILIC LUBRICITY COATING FOR MEDICAL DEVICES COMPRISING A HYBRID TOP COAT

(75) Inventors: Dachuan Yang, Plymouth, MN (US); Lixiao Wang, Maple Grove, MN (US); Joel Stanslaski, New Hope, MN (US); Liguang Tang, Plymouth, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/822,973

(22) Filed: Mar. 30, 2001

(65) Prior Publication Data

US 2001/0027299 A1 Oct. 4, 2001

Related U.S. Application Data

(63) Continuation-in-part of application No. 09/728,589, filed on Dec. 1, 2000, which is a continuation of application No. 09/316,502, filed on May 21, 1999, now Pat. No. 6,176,849.

(51) Int. Cl.$^7$ ............................................. A61M 25/00
(52) U.S. Cl. ..................................................... 604/265
(58) Field of Search ............................... 604/265, 266, 604/264, 96.01, 101.01; 427/1, 2.11, 2.12; 606/191–194

(56) References Cited

U.S. PATENT DOCUMENTS

| | | |
|---|---|---|
| 2,814,296 A | 11/1957 | Everett |
| 3,566,874 A | 3/1971 | Sheperd et al. |
| 4,026,296 A | 5/1977 | Stoy et al. |
| 4,100,309 A | 7/1978 | Micklus et al. |
| 4,119,094 A | 10/1978 | Micklus et al. ......... 128/132 R |
| 4,248,685 A | 2/1981 | Beede et al. |
| 4,373,009 A | 2/1983 | Winn |
| 4,447,590 A | 5/1984 | Szycher |
| 4,459,317 A | 7/1984 | Lambert ......................... 427/2 |
| 4,459,318 A | 7/1984 | Hyans |
| 4,487,808 A | 12/1984 | Lambert .................. 428/423.1 |
| 4,585,666 A | 4/1986 | Lambert ........................ 427/2 |
| 4,588,398 A | 5/1986 | Daugherty et al. |
| 4,642,267 A | 2/1987 | Creasy et al. ............... 428/413 |
| 4,729,914 A | 3/1988 | Kliment et al. ............... 428/36 |
| 4,876,126 A | 10/1989 | Takemura et al. |
| 4,921,483 A | 5/1990 | Wijay et al. |

(List continued on next page.)

FOREIGN PATENT DOCUMENTS

| | | |
|---|---|---|
| EP | 0 338 418 A1 | 10/1989 |
| EP | 0 380 102 | 8/1990 |
| EP | 0 480 809 A2 | 4/1992 |
| EP | 0 519 604 A2 | 12/1992 |
| EP | 0 693 293 A1 | 1/1996 |
| WO | 91/08790 | 6/1991 |
| WO | 94/27665 | 8/1994 |
| WO | 96/09086 | 3/1996 |

OTHER PUBLICATIONS

U.S. patent application Ser. No. 09/728,589, Yang et al., filed Dec. 1, 2000.

(List continued on next page.)

*Primary Examiner*—Manuel Mendez
(74) *Attorney, Agent, or Firm*—Vidas, Arrett & Steinkraus

(57) ABSTRACT

The present invention relates to a medical device for insertion into the body wherein the device has at least one surface which periodically comes into contact with a second surface. The first surface comprises an improved lubricious coating having a first hydrogel layer and a second hydrophobic top coating which prevents the hydrogel coating from prematurely absorbing too much moisture. The hydrophobic top coating comprises at least one hydrophilic surfactant which acts as a carrier to facilitate removal of the hydrophobic top coating upon entry into an aqueous environment.

24 Claims, 3 Drawing Sheets

U.S. PATENT DOCUMENTS

| | | |
|---|---|---|
| 4,990,357 A | 2/1991 | Karakelle et al. .............. 427/2 |
| 5,026,607 A | 6/1991 | Kiezulas |
| 5,041,100 A | 8/1991 | Rowland et al. |
| 5,061,424 A | 10/1991 | Karimi et al. .............. 264/171 |
| 5,061,777 A | 10/1991 | Yoda et al. .................... 528/61 |
| 5,077,352 A | 12/1991 | Elton .......................... 525/409 |
| 5,084,315 A | 1/1992 | Karimi et al. |
| 5,091,205 A | 2/1992 | Fan |
| 5,100,381 A | 3/1992 | Burns |
| 5,135,516 A | 8/1992 | Sahatjian et al. |
| 5,160,790 A | 11/1992 | Elton .......................... 428/412 |
| 5,179,174 A | 1/1993 | Elton .......................... 525/409 |
| 5,229,211 A | 7/1993 | Murayama et al. |
| 5,266,359 A | 11/1993 | Spielvogel |
| 5,272,012 A | 12/1993 | Opolski |
| 5,290,585 A | 3/1994 | Elton ............................ 427/2 |
| 5,395,666 A | 3/1995 | Brindle |
| 5,441,488 A | 8/1995 | Shimura et al. |
| 5,452,726 A * | 9/1995 | Burmeister et al. ......... 600/585 |
| 5,490,839 A | 2/1996 | Wang et al. |
| 5,503,631 A | 4/1996 | Onishi et al. |
| 5,509,899 A | 4/1996 | Fan et al. |
| 5,531,715 A | 7/1996 | Engelson et al. |
| 5,576,072 A | 11/1996 | Hostettler et al. .......... 427/532 |
| 5,656,289 A | 8/1997 | Cho et al. |
| 5,662,960 A | 9/1997 | Hostettler et al. ........... 427/2.3 |
| 5,670,558 A | 9/1997 | Onishi et al. |
| 5,688,855 A | 11/1997 | Stoy et al. .................. 524/505 |
| 5,693,034 A | 12/1997 | Buscemi et al. |
| 5,746,745 A * | 5/1998 | Abele et al. ................. 604/265 |
| 5,749,837 A | 5/1998 | Palermo et al. |
| 5,792,415 A | 8/1998 | Hijlkema |
| 5,837,313 A | 11/1998 | Ding et al. |
| 5,849,209 A | 12/1998 | Kindt-Larsen et al. |
| 5,849,368 A | 12/1998 | Hostettler et al. .......... 427/536 |
| 5,919,570 A * | 7/1999 | Hostettler et al. ........ 428/423.1 |
| 6,017,577 A | 1/2000 | Hostettler et al. ......... 427/2.12 |
| 6,030,656 A | 2/2000 | Hostettler et al. ........... 427/2.3 |
| 6,040,058 A | 3/2000 | Hostettler et al. .......... 428/457 |
| 6,046,143 A | 4/2000 | Khan et al. .................. 508/208 |
| 6,064,900 A * | 5/2000 | Vadgama et al. ............ 600/345 |
| 6,071,266 A | 6/2000 | Kelley ......................... 604/265 |
| 6,080,488 A | 6/2000 | Hostettler et al. ........ 428/423.3 |
| 6,120,904 A | 9/2000 | Hostettler et al. ........ 428/423.3 |
| 6,176,849 B1 * | 1/2001 | Yang et al. .................. 604/265 |

OTHER PUBLICATIONS

U.S. patent application Ser. No. 09/316,502, 6,176,849, Yang et al., filed May 21, 1999.

Szycher, Ph.D., Michael, "Biostability of Polyurethane Elastomers: A Critical Review", *Blood Compatible Materials and Devices Perspectives Towards the 21st Century*, Chapt. 4, pp 33–85 (1991).

Tecoflex® brochure.

Gantrez® AN Copolymer brochure.

Author unknown, "Release Agents", 14:411–420 (date unknown).

* cited by examiner

HYDROPHILIC LUBRICITY COATING FOR MEDICAL DEVICES COMPRISING A HYBRID TOP COAT

CROSS-REFERENCE TO RELATED APPLICATIONS

This case is a continuation-in-part of copending U.S. patent application Ser. No. 09/728,589 filed Dec. 1, 2000 which is a continuation of Ser. No. 09/316,502 filed May 21, 1999 now U.S. Pat. No. 6,176,849 issued Jan. 23, 2001.

FIELD OF THE INVENTION

This invention relates to a coating lubricity for insertable or implantable medical devices having improved lubricity, which comprises a first coating of a water swellable polymeric substance and a second coating having a hydrophobic component and a hydrophilic surfactant. These coatings find particular utility for the balloon portion of a catheter device.

BACKGROUND OF THE INVENTION

Water soluble, biocompatible compounds that impart lubricity to the surface of otherwise non-lubricious materials are desirable for use on medical devices which are inserted or implanted into the body. Such medical devices may include catheters that are utilized to deliver a stent, stent-graft, graft or vena cava filter, balloon catheters, other expandable medical devices and so forth. The industry has turned to hydrophilic lubricious coatings in order to overcome problems with commonly used hydrophobic coatings such as silicone, glycerine or olive oil.

Hydrophobic coatings have been known to bead up and run off when exposed to an aqueous environment, lose initial lubricity rapidly, and lack abrasion resistance. Residual amounts of silicone have also been known to cause tissue reaction and irritation in patients. The loss of lubricity can lead to discomfort during insertion into a patient, and damage to blood vessels and tissues due to frictional forces during insertion or removal of the device.

One class of polymeric substances which dissolve or swell in an aqueous environment, often referred to as "hydrogels," are capable of manifesting lubricity while in a wet state, and are popularly utilized as lubricious coatings for medical devices. When hydrated, these substances have low frictional forces in humoral fluids including saliva, digestive fluids and blood, as well as in saline solution and water. Such substances include polyethylene oxides, optionally linked to the substrate surface by urethane or ureido linkages or interpolymerized with poly(meth)acrylate polymers or copolymers; copolymers of maleic anhydride; (meth)acryl amide polymers and copolymers; (meth)acrylic acid copolymers; poly(vinyl pyrrolidone) and blends or interpolymers with polyurethanes; and polysaccharides.

These water soluble coating materials, while popular because they provide excellent lubricity and biocompatibility, may be sensitive to moisture.

A problem associated with the moisture sensitivity of such hydrogels is that they may prematurely uptake ambient moisture and become sticky or tacky. This can result in undesirable adhesion of the medical device to itself, to other devices if mass packaged, or to any other surface to which it comes in contact during sterilization or storage. In the case of dilatation balloons, after sterilization or storage these hydrogel coatings can become delaminated from the polymeric surface upon expansion of the balloon because the folded sections stick to one another by cross-polymerization or bridging.

In the case of metal wires, such as guide wires, which may be packaged in rolls, the "self adhesive" effect can lead to removal of some of the coating, leaving pinholes or complete failure of the coating from the surface of the wire as it is uncoiled.

These problems are discussed in U.S. Pat. No. 5,509,899 issued Apr. 23, 1996 to Fan et al. Fan et al. teaches a medical balloon and catheter which is wrapped and folded upon itself and in which the balloon is free of bridging and adhesion between abutting surfaces. The balloon has a base of a continuous polymeric surface which is expandable. On the polymeric surface is disposed a lubricious, biocompatible hydrogel coating and a thin, lubricious, blood-compatible coating is disposed on the hydrogel coating and adheres to it to prevent abutting surfaces of the folded polymeric surfaces from adhering to each other during inflation and to prevent delamination of the hydrogel coating and/or rupture of the balloon. Preferably, the blood-compatible coating is polyethylene glycol, methoxy polyethylene glycol or mixtures thereof having a molecular weight of between about 100 and 20,000 grams per gram mole. The blood-compatible coating is applied as an anti-blocking agent. See column 2 lines 18 to 37.

The present inventors have found a coating for medical devices which avoids the aforementioned problems comprising a first coating of a hydrogel polymeric substance, and a second coating of a hydrophobic silicon having a hydrophilic surfactant which can impede blocking or sticking of two surfaces for improved lubricity, as well as the shelf life.

SUMMARY OF THE INVENTION

The present invention relates to a medical device for insertion into the body wherein the device has at least one surface which periodically comes into contact with a second surface. The first surface comprises an improved lubricious coating having a first hydrogel layer and a second hydrophobic top coating which prevents the hydrogel coating from prematurely absorbing too much moisture. The hydrophobic top coating comprises at least one hydrophilic surfactant which acts as a carrier to facilitate removal of the hydrophobic top coating upon entry into an aqueous environment.

The medical device may be insertable or implantable, and/or it may be an expandable medical device such as a balloon catheter, or it may be an elongated device designed for manipulation within the body.

DETAILED DESCRIPTIONS OF THE PREFERRED EMBODIMENTS

Figure 1:
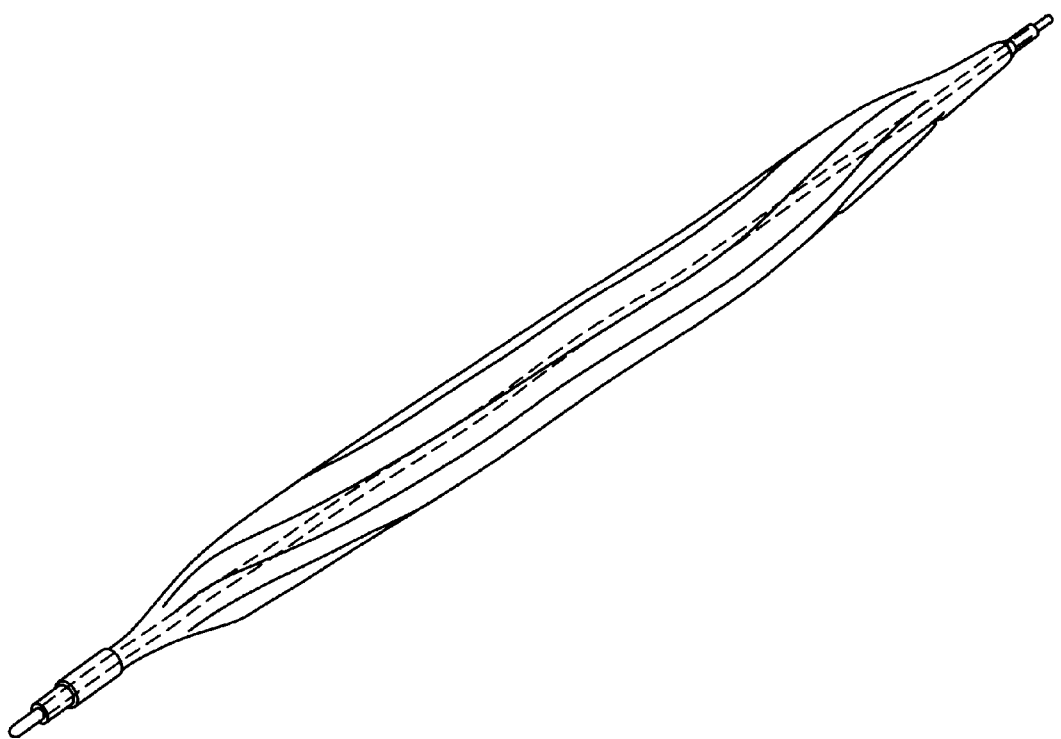
FIG. 1 is a side view of a catheter with a balloon tightly wrapped and folded for insertion for a medical procedure.
Figure 2:
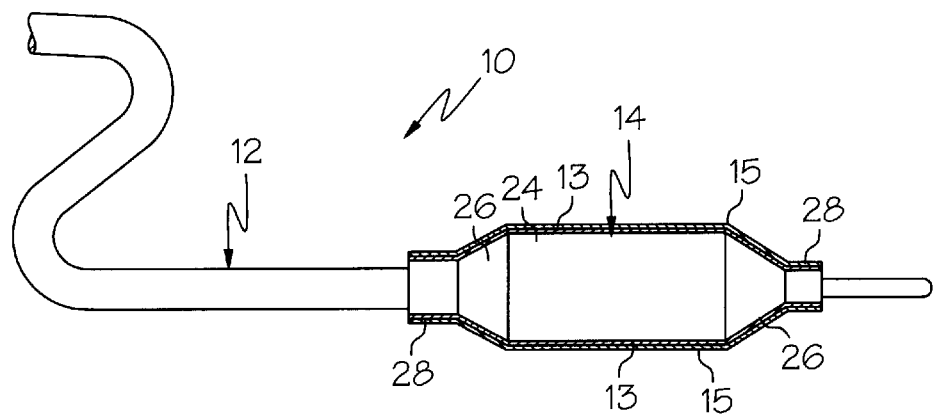
FIG. 2 is a perspective view of a dilatation catheter that includes the inflated coated balloon of FIG. 1.

FIG. 2 is a schematic representation of an inflated dilatation balloon catheter of the present invention, illustrated generally at 10. The inflated balloon 14 is mounted at the distal end of an elongated flexible shaft 12. Except as noted herein, catheter 10 is conventional in its construction, providing a lumen communicating with the interior of the balloon 14, for inflation and deflation of the balloon, and other optional features conventional in the dilatation catheter art. The balloon 10, has an inflated configuration, illustrated in FIG. 2 and is made up of three main portions: the body 24, the cones 26 and the waist portions 28. FIG. 1 illustrates the lubricious hydrogel coating 13 and the hydrophobic top coating 15 on the body 24, the cones 26 and the waist 28. FIG. 2 illustrates a coating which is of a uniform thickness on all parts of the balloon. A coating gradient could also be established whereby the coating weight on the body 24, is less than the coat weight on the cones and the coating is thickest on the cone portion closest to the waist and on the waist itself.

Balloons are typically made by a process by extruding the balloon material into a tubular preform, blow molding the balloon, and annealing. The tubular preform may be stretched prior to blowing. The coatings of the present invention may be applied to the tubular preform prior to blowing. In this case, the coating will form a gradient whereby the coat weight will be inversely proportional to the amount of expansion the different parts of the balloon goes through. For instance, the lowest coat weights will be found on the body of the balloon which expands the most. The coat weight will be the heaviest on the waist portion which may expand only slightly, stay the same, or even decrease slightly in size.

Figure 3:
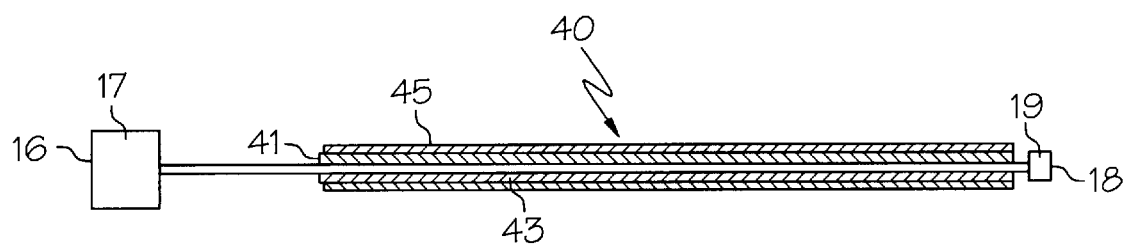
FIG. 3 is a schematic representation of an elongated medical device of the invention.

FIG. 3 is a schematic representation of an elongated medical device which may be a guide wire, catheter, cannula, fiber optic device and the like. Device 40 extends between proximal end 16 and distal end 18 and includes an elongate body 41. A control mechanism 17 may optionally be provided at or near the proximal end of device 40 to facilitate manipulation of the device and/or activation of functional structure provided on the device, such as drug delivery or balloon inflation lumen. Device 40 may also optionally be provided with a functional structure 19, such as an inflatable balloon, deployable stent, drug delivery mechanism, or the like, typically at or near the distal end 18.

Very little limitation is placed on the material for the elongate body 41. Most devices will have a relatively flexible body, such as when the device 40 is a catheter or guide wire. However, the invention may also be used with inflexible transcutaneous devices such as a needle. Body 41 may be made of organic high polymer materials such as polyamide, polyester, polyvinyl chloride, polystyrene, polyacrylate, polymethacrylate, polyacrylonitrile, polyacrylamide, polyethylene, polypropylene, polyurethane, polyvinyl acetate, silicone resins and copolymers and blends thereof. However, various inorganic materials such as glass, ceramic, stainless steel, and super elastic metal or shape memory alloy such as Ni—Ti, and the like may be employed on part or all of body 41. Body 41 may also be formed as a composite of different materials which are laminated together. Depending on the nature of the specific device 40, body 41 may be provided with one or more lumens, electrical connectors, optical fibers or the like, as is well known in the medical art.

One specific embodiment of device 40 is a balloon catheter for angioplasty and the like, in which case functional structure 19 will include an inflatable balloon, located very near the distal end 18 of device 40. The elongate body 41 will be a flexible tube, typically polymeric, containing at least an inflation fluid lumen for the balloon and a control mechanism 17 located at the proximal end 16 of device 40 of conventional design will be provided for manipulating the catheter to the desired site in the body and for causing the balloon to inflate and deflate as desired. Such a catheter may also be provided with a soft distal tip as part of functional structure 19 to facilitate maneuvering the balloon to cross a lesion and/or a guide wire lumen to allow the catheter to be inserted over a guide wire.

Another specific embodiment of device 40 is a guide wire in which case body 41 may be a metal wire. There may not be any control mechanism 17 present at the proximal end 16 and the distal functional structure 19 at the distal end 18 may simply be a conventional coiled or soft polymeric tip.

The coated portions may be body 41 of device 40 which is coated in FIG. 3 with a hydrogel coating 43 and the hydrophobic top coating 45 of the present invention.

If the functional structure 19 is a dilatation balloon, the balloon may also be coated as shown generally at 10 in FIG. 2 wherein the inflated balloon is coated with hydrogel coating 13 and hydrophobic top coating 15.

Figure 4:
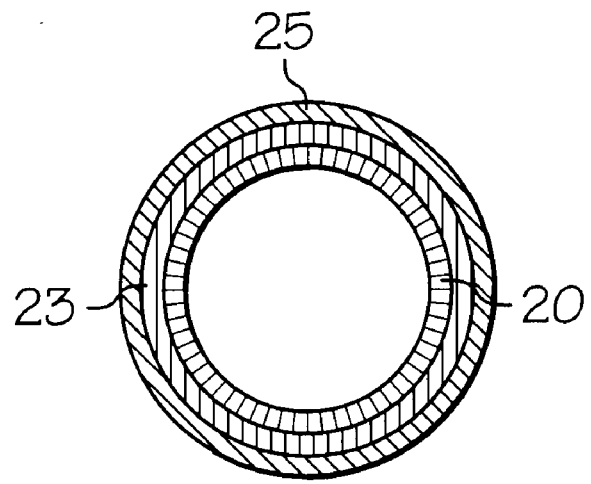
FIG. 4 is an enlarged cross-sectional view of the coatings as viewed on either the balloon of FIG. 2 or on an elongated medical device as in FIG. 3.

FIG. 4 is a schematic cross-sectional representation of a balloon wall 20 having a lubricious hydrogel coating 23 disposed thereon and a hydrophobic top coat 25 disposed on the hydrogel coating 23. The wall may be formed from any flexible polymeric substance. In some preferred embodiments the balloon wall if formed from polyether block amides, such as Pebax® 7033 or 7233; polyester block ethers such as Arnitel® EM 40; polyethylene terephthalate; and nylon. FIG. 4 may also be representative of a coated tubular preform or an inner lumen for carrying fluids.

Figure 5:
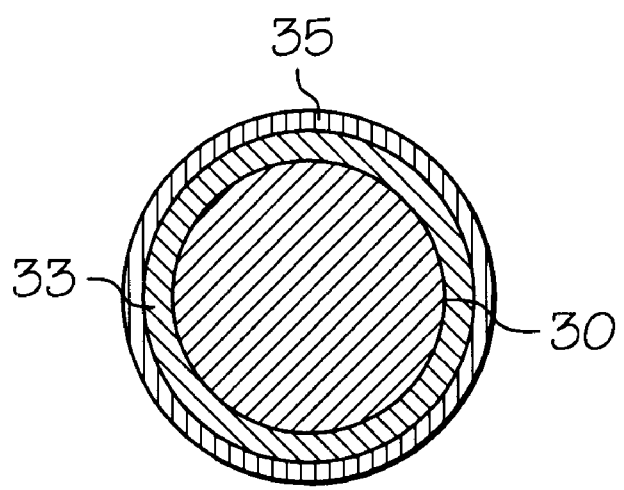
FIG. 5 is a schematic cross-sectional representation of a guide wire having a lubricious hydrogel coating with a hydrophobic top coat disposed thereon.

FIG. 5 is a schematic cross-sectional representation of a guide wire 30 having a lubricious hydrogel coating 33 disposed thereon and a hydrophobic top coat 35 disposed on the hydrogel coating 33. The guide wire may be formed from a metal and may preferably be a shape memory alloy such as Ni—Ti alloy.

FIG. 4 and FIG. 5 are expanded views of such medical devices and are not meant to limit the ratio of the coat weight of the hydrogel coating to the top coat. The coat weights may vary.

The hydrogel coating has a thickness between about 1 and 10 μm. The hydrogel coating is a lubricious, hydrophilic material which has the ability to dissolve or swell upon exposure to an aqueous type of environment. Water soluble polymers can be used which are generally chain-structured, non-crosslinked polymers having a hydrophilic group such as —OH, —CONH$_2$, —COOH, —NH$_2$, —COO—, SO$_3$, AND NR$_3{}^+$, where R is alkyl or hydrogen.

Natural water soluble polymers may also be utilized such as carboxymethyl cellulose, methyl cellulose, hydroxyethyl cellulose and hydroxypropyl cellulose, heparin, dextran, modified dextran and chondroitin sulphate.

Synthetic water soluble polymers include the polyalkylene glycols and polyoxyalkylene glycols such as polyethylene oxide, polyethylene oxide/polypropylene oxide copolymers and methoxypolyethylene oxide; copolymers of maleic anhydride including methyl vinyl ether-maleic anhydride copolymers; pyrrolidones including poly (vinylpyrrolidone); acryl amides including poly(N-alkylacrylamide); poly(acrylic acid); poly(carboxylic acids); poly(vinyl alcohol); poly(ethyleneimine); polyamides; water soluble nylons; polyurethanes; and so forth.

Derivatives of any of these polymers may be utilized providing that enough of the basic structure of the polymers above that provides water sensitivity, solubility or dispersibility is retained allowing the polymer to uptake enough water to swell or partially dissolve enough upon exposure to moisture to provide lubricity in such a way to reduce frictional forces between the surface it is coated on and another surface such as tissue, metal or polymeric surfaces. Water insoluble derivatives may be employed as long as they have the freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above-mentioned water soluble polymers. Also used are polymers crosslinked with substances having more than one reactive functional group such as diazonium, azide, isocyanate, acid chloride, acid anhydride, imino carbonate, amino, carboxyl, epoxy, hydroxyl, and aldehyde groups.

Copolymers with vinyl groups, acrylic acid, methacrylic acid, diene compounds and maleic anhydride have been preferably utilized.

Carboxylic acid-containing polymers may be preferably used as coating materials in the invention.

In another preferred embodiment, a hydrogel of polyethylene oxide may be captured in an interpenetrating crosslinked acrylic polymer network by polymerizing a mixture of an acrylic monomer composition comprising a monomer having plural (meth)acrylate groups and polyethylene oxide, thereby providing a hydrogel coating. The lubricity of such a coating can be modified, for instance by reaction of the active hydrogen groups of the polyethylene oxide with an active hydrogen reactive compound such as an isocyanate, an acid chloride, an anhydride, an alkyl halide, etc. Varying the ratio of monomer to polyethylene glycol over the length of the coating can also be used to create a lubricity coating gradient.

The hydrogel coating is then top coated or treated with a hydrophobic coating. In one specific embodiment, the hydrophobic coating is silicone based. These silicones may be of the siloxane type. In one specific embodiment of the present invention, Dow Corning® DC 360 is utilized as the hydrophobic silicone agent. Other synthetic hydrophobic compounds useful to the present invention include chlorotrifluoroethylene (CTFE oil), polyphenyl ethers and so forth.

In other embodiments, the hydrophobic coating is based on a naturally occurring composition including, for instance, olive oil, paraffine oil, corn oil, sesame oil, sweet almond oil, hydrogenated vegetable oil, purcellin oil, apricot oil, mineral oil, lanolin oil, fish oil, cotton seed oil, glycerine, and so forth. One of skill in the art would recognize that there are other selections available for use herein.

The hydrophilic surfactants useful to the present invention include polyoxyethylene modified silicones which are nonionic surfactants useful for addition to the hydrophobic top coating. These include the Silwet® surfactants manufactured by Witco. These are linear polydimethylsiloxanes grafted with EO and PO through hydrozylation, or through the Si—O—C bonds. By varying the ratio of EO and PO and by varying the molecular weights, a broad range of Silwet® surfactants are available on the market which offer unique properties and performance advantages over other conventional organic surfactants. A hydrophilic surfactant is admixed with the hydrophobic silicone by dissolving in a cosolvent or a mixture of solvents. The surfactants have both a hydrophobic portion, usually a long chain hydrocarbon, and a hydrophilic portion allowing them to have some compatibility with the silicone agent and some water solubility as well. The hydrophilic surfactant may be an alkylene glycol or a polyoxyalkylene glycol of the ethylene oxide/propylene oxide copolymer type. Specific examples include the Pluronic® and Pluronic® R ethylene oxide(EO)/propylene oxide(PO) block copolymer surfactants available from BASF. Pluronic® surfactants are blocks of EO/PO/EO having from about 10% to about 80% EO. Pluronic® R surfactants are PO/EO/PO blocks. The molecular weights ranges from about 1800 to about 8500 g/mole and have from about 10% to about 80% EO. The reversed hydrophobic and hydrophilic blocks create differences in performance versus the EP/PO/EO blocks. Examples include Pluronic® F127, Pluronic® P105, or Pluronic® L44 which are all EP/PO/EO triblock copolymers.

Other useful hydrophilic surfactants include polyethylene oxide based block copolymers such as the Tetronic® series of surfactants made by BASF. Tetronic® surfactants are tetrafunctional block copolymers derived from the sequential addition of EO and PO by ethylene diamine. The amine moiety in these surfactants provides slightly cationic properties and contributes to thermal stability. The molecular weight of these compounds ranges from about 2600 to about 20,500 g/mole and they contain from about 10% to about 80% EO.

In other embodiments of the present invention, polyoxyethylene castor oil derivatives are utilized as the hydrophilic surfactant. Polyoxyethylene castor oil derivatives are a series of materials obtained by reacting various amounts of ethylene oxide with either castor oil or hydrogenated castor oil. Several different types of materials are commercially available, one series being the Cremophor® series from BASF including Cremophor® EL 35 and Cremophor® RH 40.

Nonionic hydrophilic surfactants useful to the present invention include decyl and tridecyl alcohol ethoxylates. Commercially available examples include the Iconol® series made by BASF including Iconol® NP and Iconol® OP. These compounds have from about 4% to about 70% by weight EO concentration. Other similar nonionic surfactants include Icomeen® fatty amine ethoxylate surfactants; Klearfac® phosphate ester surfactants; Plurafac® linear alcohol alkoxylate surfactants; Pluracol® E polyethylene glycols; Pluracol® W polyalkoxylated polyethers; Sokalan® CP acrylic acid or maleic anhydride copolymers; and so forth.

The solvent mixture may be a blend that will solubilize both the hydrophobic silicone agent and the hydrophilic surfactant. This cosolvent mixture may preferably include isopropanol and aliphatic hydrocarbons such as heptane or hexane, for instance. Other useful polar solvents may include ethanol, methanol, stearyl alcohol, ethylene glycol, propylene glycol, glycerin, water and so forth. Other useful non-polar solvents include mineral spirits; aromatic hydrocarbons such as toluene and xylene; chlorinated hydrocarbons such as perchloroethylene, methylene chloride, chloroform, carbon tetrachloride, 1,1,1-trichloroethane; fluorocarbons and so forth. The hydrophobic agent and the hydrophilic surfactant may then be coated out of this cosolvent mixture.

The hydrophilic surfactant is used at concentrations in solvent of from about 1% to about 90%, preferably from about 1% to about 30% and most preferably from about 5% to about 20%. The hydrophobic agent is used at concentrations in solvent from about 1% to about 30%, preferably from about 1% to about 10% and most preferably from about 2% to about 5%.

The hydrophobic compound and the hydrophilic surfactant may be dissolved in a solvent or mixture of solvents. Useful solvents include alcohols, aliphatic hydrocarbons, aromatic hydrocarbons, chlorinated solvents, esters, glycols, glycol ethers, ketones, and so forth. Polar solvents include alcohols, glycols, water and so forth. Specific examples include ethanol, methanol, isopropyl alcohol (IPA), stearyl alcohol, ethylene glycol, propylene glycol, glycerin, water, methylethyl ketone (MEK) and so forth. Non-polar solvents include aliphatic hydrocarbons such as heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits and so forth. Typically, a cosolvent mixture of a polar solvent, such as isopropanol, and a nonpolar solvent, such as heptane, may be utilized.

One specific top coat of the present invention includes sesame oil as the hydrophobic component, Cremophor® EL 35 (polyoxyethylene castor oil derivative) or Pluronic L44 (ethylene oxide(EO)/propylene oxide(PO)/ethylene oxide (EO) tri block copolymer) as the hydrophilic component in a heptane/isopropanol solvent blend.

Another specific top coat of the present invention includes Dow Corning DC 360 silicone and Silwet® polyoxyethylene modified silicone surfactant in n-heptane.

These coatings may be utilized on any insertable or implantable medical instruments or devices including guide wires, catheters, dilatation balloons, stents, stent grafts, grafts, vena cava filter, inflation lumens and so forth.

Balloons are typically made of polymeric materials including nylon, Selar®, polyether-polyester block copolymers (i.e. Hytrel®, Pebax®, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof. Such materials are typically inherently non-lubricious making it necessary to add some type of lubricious coating to the surface in order to advance the device through the blood vessel more easily.

One specific embodiment of a medical device of the present invention is a balloon catheter for angioplasty and the like, in which case the functional structure will include an inflatable balloon, located very near the distal end of the device. The elongate body will be a flexible tube, typically polymeric, containing at least an inflation fluid lumen for the balloon. A control mechanism of the conventional design will be provided for manipulating the catheter to the desired target site in the body and for causing the balloon to inflate and deflate as desired. Such a catheter may also be provided with a soft distal tip and/or guide wire lumen to allow the catheter to be inserted over a guide wire.

Another specific embodiment of a medical device of the present invention is a guide wire in which case the body may be a metal wire, such as a Ni—Ti alloy. In this case, there may not be any control mechanism present at the proximal end and the distal functional structure may be a conventional coiled or soft polymeric tip.

The coating of the present invention may be utilized on any or all of the structures of the medical device. These coatings have found particular utility for dilatation balloons and for guide wires. In the case of the dilatation balloon, the coating will prevent the polymeric surfaces from adhering and sticking together in the folded state. A hydrogel coating, by itself, may bridge and ultimately cause rupturing of the balloon upon inflation. The hydrophobic top coat having the hydrophilic surfactant, will improve the shelf life of the folded balloon by preventing the hydrogel coating from up taking too much moisture and bridging.

In the case of guide wire lumens, large lengths of the wire are often rolled up together with adjoining surfaces in contact with one another. The coatings of the present invention prevent the hydrogel coating from bridging and sticking to itself which can ultimately cause coating to be pulled away from the wire surface thereby leaving bare wire which in turn can lead to discomfort during insertion into a patient and ultimately tissue damage.

The device is first coated with the hydrogel coating. This coating provides the lubricity. Hydrogel coatings typically improve lubricity by taking up water which allows them to become slippery and lubricious.

After coating, the device is preferably dried using heat and subsequently exposed to UV light, for instance, to crosslink or cure the hydrogel coating.

The device is then coated with the secondary coating or top coating which comprises the hydrophobic silicone compound and the hydrophilic surfactant. This is coated out of solution. This top coating protects the hydrogel coating from absorbing too much ambient moisture and becoming sticky. In the case of a dilatation balloon which is folded upon itself prior to use, the bridging or adhesion of the coating can be so severe that the balloon ruptures upon inflation. Upon insertion of the device into a bodily orifice, and exposing it to bodily fluids, the hydrophilic portion of the surfactant allows the top coating to be washed away. The biocompatibility of the surfactant allows it to be easily eliminated from the body without excessive tissue irritation. The surfactant, with its hydrophobic portion, conveys the silicone agent with it, thereby removing the top coating and allowing the lubricious coating to swell upon exposure to the aqueous environment.

The medical device, i.e. balloon, may be coated by dipping, spraying, wiping, and so forth.

The noncuring coatings of the present invention provide numerous advantages over other systems. One advantage is that they allow for a one-step, more simplified coating operation over that of a curing system. It is also possible to eliminate the bio-tube further simplifying operations.

The coatings of the present invention can be dried at room temperature and require only short drying times. They are stable in air for long periods of time. Further, spillage can be easily removed from counters or floors, for instance, using water or isopropanol.

The following non-limiting examples further illustrate embodiments of the present invention.

TEST METHODS

1. Catheter Opening Pressure

Measured using a Final Functional Burst Machine which has a 0.014" full length test mandrel. The machine is designed specifically for balloon catheter testing. A glycerol/water solution is first used to prime the burst machine. A catheter is prepared per standard balloon preparation procedures. The catheter manifold is connected to the final functional burst machine. Timer 1 (pressure) is set for 5 minutes, timer 2 (vent) for 0 seconds, and timer 3 (vacuum) for 0 seconds. The machine continuously ramps in pressure until the balloon opens. The machine is adjusted to a pressure of 5 psi and held for 10 seconds. The pressure is then increased by 5 psi every 10 seconds until the balloon opens. The pressure that is required to fully open the balloon is the opening pressure.

2. Balloon Friction

Measures the friction of catheter materials both with and without coating applied to them. A 3½" section is cut from a PTCA catheter. The area from which the catheter sample comes is recorded as well as the type of material from which it is made. A mandrel is inserted through the center of the catheter test section in order to prevent the tubing from yielding to the constant vertical load. The catheter sample is placed on the test rack and secured in place with tape. The rack assembly with the catheter mounted to it is then placed in a water bath at 37° C. and clamped to the drive beam. A latex rubber pad is inserted on the arm of the load cell. The arm is lowered down onto the catheter test sample and the brass weight is held over the latex rubber pad with a string. The water level in the bath should cover the test sample by 0.5 cm. A computer program then runs a motor drive back and forth 129 times and the data from the load cell is automatically recorded with a PC. The section of catheter is then placed on a support bridge that moves back and forth under a weighted latex rubber pad. The rubber pad is coupled to a load cell by a mechanical arm. As the catheter moves back and forth, the frictional forces between the latex rubber pad and the PTCA catheter are recorded by a data acquisition system. Testing is conducted in a water bath heated to 37° C.

EXAMPLES

Hydrogel Coating 1

A catheter useful for angioplasty having a balloon with a 3.0 mm diameter and a length of 20 mm was used in this example. The balloon was coated with a high molecular weight polyethylene oxide coating which had a 2,2'-azobis isobutyro-nitrile catalyst (both from Aldrich Chemical). The coating was subsequently dried and cured under UV radiation to facilitate crosslinking of the polyethylene oxide.

Hydrogel Coating 2

A catheter useful for angioplasty having a small balloon with 2.5 mm diameter and a length of 14 mm was used in this example. The balloon was coated with a 3% solution of a high molecular weight poly(vinyl pyrrolidone) with a dibutyltin dilaurate catalyst (both from Aldrich Chemical) in heptane by dipping. The coating was exposed to heat in a 50° C. oven for 5 hours to facilitate crosslinking of the polymer.

Slipcoat 1

Slipcoat 1 is a mixture of DOW CORNING DC-360 hydrophobic silicone with DOW CORNING MDX4-4159 at a ratio of 2:1 and a concentration of 4.5% in heptane. MDX4-4159, according to the technical data sheet, is a solution having 34% Stoddard Solvent, 15% isopropyl alcohol, 1% dimethyl cyclosiloxanes, and 50% dimethoxy silyl dimethyl aminoethyl amino propyl silicone polymer (all constituents are expressed in %, by weight). No hydrophilic surfactant is present.

Slipcoat 2

A solution of 4% Dow Corning® DC-360 polydimethyl siloxane and 10% Pluronic® 31 R1, PO/EO/PO block copolymer hydrophilic surfactant, from BASF in 1:1 (volume) isopropanol and heptane cosolvent mixture was prepared.

Slipcoat 3

Slipcoat 3 is a solution of 4% polydimethylsiloxane (DC-360) and 10% Cremophor® EL 35 as the hydrophilic surfactant in a 1:1 volume cosolvent mixture of isopropanol and heptane.

Slipcoat 4

Slipcoat 4 is a mixture of Pluronic® 17R4 EO/PO/EO triblock copolymer surfactant and silicone oil at a ratio of 1:4 and a concentration of 15% in an 2:1 n-heptane/isopropanol solvent blend.

Slipcoat 5

Slipcoat 5 is a mixture of PLURONIC® L44 EO/PO/EO triblock copolymer surfactant and sesame oil at a ratio of 1:4 and a concentration of 10% in a 2:1 n-heptane/isopropanol solvent blend.

Slipcoat 6

Slipcoat 6 is a mixture of PLURONIC® L44 EO/PO/EO triblock copolymer surfactant and sesame oil at a ratio of 1:4 and a concentration of 5% in a 2:1 n-heptane/isopropanol solvent blend.

Example 1

The balloon coated with Hydrogel 1, was inflated under low pressure (about 2 atmospheres), dipped into a solution of slipcoat 2, above, for 10 seconds, removed, and dried in a 50° C. oven for 2 hours. The balloon is then deflated and placed into a 2.0 mm diameter balloon protector and ethylene oxide sterilized in a 13 hour cycle.

Comparative A

A balloon is coated only with the hydrogel coating 1.

Comparative B

A balloon is coated with the hydrogel coating 1 followed by slipcoat 1.

TABLE 1

|  | Example 1 | Comparative A | Comparative B |
| --- | --- | --- | --- |
| Balloon Opening Pressure (psi) | 25 | 60 | 29 |
| Lubricity (grams) | 6 | 5.5 | 11 |

As can be seen from the data, the balloon coated with the method of the present invention, Example 1, exhibited the best overall performance of low opening pressure and low frictional forces.

Example 2

A balloon was coated with hydrogel coating 1, above, was then further treated with a coating of slipcoat 3. The same procedure for coating and drying was followed as in Example 1. Comparative examples A and B were again prepared as above. The following results were obtained.

Comparative C

A balloon coated with hydrogel coating 1 and followed with a top coat of slipcoat 1 based on polydimethylsiloxane.

TABLE 2

|  | Example 2 | Comparative A | Comparative C |
|---|---|---|---|
| Balloon Opening Pressure (psi) | 27 | 58 | 24 |
| Lubricity (grams) | 6.5 | 6.0 | 15.0 |

Example 2 exhibited the overall best performance of low opening force and low frictional forces.

Example 3

A balloon was coated with hydrogel 1 followed by treatment with slipcoat 4. The hydrogel coated balloon was treated with this second coating as in Examples 1 and 2.

Comparative Example D

Hydrogel Coating 2 alone.

Comparative Example E

Hydrogel Coating 2 followed with a top coating of slipcoat 1.

TABLE 3

|  | Example 3 | Comparative D | Comparative E |
|---|---|---|---|
| Balloon Opening Pressure (psi) | 26 | 43 | 26 |
| Lubricity (grams) | 6.9 | 6.8 | 17.4 |

Example 3 exhibited lower opening force and comparable lubricity to the balloon coated only with hydrogel coating 2 (comparative D) and much lower lubricity and comparable opening pressure to Comparative E. It exhibited overall better properties than either of the comparative examples.

Example 4

Comparative Examples F and G

Comparative example F was prepared by coating a PEBAX polyether block amide elastomer catheter balloon (2 mm diameter, 20 mm length) was coated with hydrogel coating 1 alone. Comparative example G was prepared by coating the same type of balloon with hydrogel coating 1 followed by slipcoat 1. Example 4 was prepared by coating the same type of balloon catheter with hydrogel 1 followed by slipcoat 5. The balloons were then tested for lubricity (grams force) and the results for each were compared. Between 3 and 6 units (i.e. balloons) were measured with 11 measurements being taken for each balloon. An average was calculated for all of the data. Comparative example G exhibited the highest friction while example 4 with the slipcoat of the present invention exhibited the lowest friction. Example 4 exhibited comparable opening pressure to comparative F but much lower opening pressure than comparative G overall exhibiting improved properties.

TABLE 4

|  | Comparative F | Comparative G | Example 4 |
|---|---|---|---|
| Balloon Opening Pressure (psi) | 18 | 55 | 21 |
| Lubricity | 6.3 | 6.9 | 16.0 |

Example 5

Comparative Example H

Example 5 was prepared by coating a PEBAX® polyether block amide catheter balloon (2 mm by 20 mm) with hydrogel coating 1 followed by slipcoat 6. Comparative H was prepared by coating the same type of catheter balloon with hydrogel coating 1 followed by slipcoat 1. All balloons had a 0.031" balloon protector. The balloon protector is a small plastic polyethylene tube used in every balloon catheter to wrap down the folded balloon. The balloon protector is removed before the catheter is used. The smaller the balloon protector, the tighter the balloon is wrapped and thus the smaller the balloon profile. This smaller profile creates higher balloon opening pressures because of how tightly the balloon is wrapped. A typical balloon opening pressure is less than 30 psi to avoid pinhole formation in the balloon or other friction-related damage. The slipcoat of the present invention provides an acceptable balloon opening force which is comparable to the state of the art.

The opening pressure (psi) was measured and averaged. Example 5 had an average opening pressure of 23±6.7 psi while comparative H had an average opening pressure of 16 psi. Opening pressures of under 30 psi are acceptable for most applications. While comparative H shows a lower opening pressure, it also has all the disadvantages of using a silicone based hydrophobic top coating whereas Example 5 has acceptably low opening pressure while it has the further advantages of utilizing a more hydrophilic top coating.

Example 6

Example 6 was prepared by coating a PEBAX® polyether block amide catheter balloon (2 mm diameter, 20 mm length) with hydrogel coating 1 followed by slipcoat 6. Comparative I was prepared by coating the same type of balloon with hydrogel coating 1 followed by slipcoat 1. The same procedure as above was used to treat the balloon. The inflated balloon was dipped in the slipcoat solution and oven dried for 10 seconds. A 0.032" balloon protector was used which is relatively larger than the one used in Example 5. The average opening pressure was 19 psi±4.2 psi. Comparative I had an average opening pressure of 10 psi±2.7 psi. Again, as above, opening pressures of less than 30 psi are considered as acceptable. Both example 6 and comparative example I exhibit very good opening pressures but example 6 has the added benefits of utilizing the more hydrophilic top coating which also has far better lubricity than the silicone based coating.

What is claimed is:

1. A medical device for insertion into the body, said device having at least one surface which periodically comes into contact with a second surface, said first surface comprising:
   a) a first lubricious hydrogel layer disposed on said first surface; and
   b) a second hydrophobic top coating comprising at least one hydrophilic surfactant.

2. The medical device of claim 1 wherein said hydrogel layer comprises a polymeric material selected from the group consisting of polyalkylene glycols, alkoxy polyalkylene glycols, copolymers of methylvinyl ether and maleic acid, poly(vinylpyrrolidone), poly(N-alkylacrylamide), poly (acrylic acid), poly(vinyl alcohol), poly(ethyleneimine), polyamides, methyl cellulose, carboxymethyl cellulose, polyvinyl sulfonic acid, heparin, dextran, modified dextran and chondroitin sulphate.

3. The medical device of claim 1 wherein said hydrogel layer comprises at least one hydrophilic polymer comprising polyethylene oxide.

4. The medical device of claim 1 wherein said hydrogel layer comprises at least one hydrophilic polymer comprising poly(vinylpyrrolidone).

5. The medical device of claim 1 wherein said hydrophobic coating comprises a hydrophobic silicone compound.

6. The medical device of claim 5 wherein said hydrophobic silicone compound is a siloxane.

7. The medical device of claim 6 wherein said siloxane is dimethyl siloxane.

8. The medical device of claim 1 wherein said hydrophobic coating comprises a naturally occurring hydrophobic compound.

9. The medical device of claim 8 wherein said hydrophobic compound is selected from olive oil, sesame oil, fish oil, cotton seed oil, paraffine oil, corn oil, sesame oil, sweet almond oil, hydrogenated vegetable oil, purcellin oil, apricot oil, mineral oil, lanolin oil, glycerine, and mixtures thereof.

10. The medical device of claim 9 wherein said hydrophobic compound is selected from olive oil, sesame oil, fish oil, cotton seed oil, and mixtures thereof.

11. The medical device of claim 1 wherein said hydrophilic surfactant is selected from the group consisting of polyalkylene glycols, alkoxy polyalkylene glycols, polyoxyethylene castor oil, and mixtures thereof.

12. The medical device of claim 11 wherein said copolymer of ethylene oxide is an ethylene oxide/propylene oxide block copolymer.

13. The medical device of claim 11 wherein said hydrophilic surfactant is a polyoxyethylene castor oil.

14. The medical device of claim 1 wherein said device is a dilatation balloon.

15. The medical device of claim 1 wherein said device is a guide wire.

16. The medical device of claim 14 wherein said balloon comprises a polymeric material selected from the group consisting of polyether block amides, polyester block ethers, polyethylene terephthalate and nylon.

17. A method for producing a medical device as in claim 1 comprising the steps of:

a) coating said device with a first coating of a lubricious hydrophilic polymeric material; and
   b) coating said device with a second coating of a hydrophobic material said hydrophobic material comprising at least one hydrophilic surfactant.

18. A medical device for insertion into the body comprising a polymeric surface which is at least periodically subjected to contact with at least one second surface said first polymeric surface comprising:

a) a first lubricious hydrophilic coating disposed on said first polymeric surface; and
   b) a second hydrophobic coating disposed on said first hydrophilic coating said hydrophobic coating comprising at least one hydrophobic silicone compound and at least one hydrophilic surfactant;

wherein said first hydrophilic coating is biocompatible and said second hydrophobic coating inhibits said first hydrophilic coating from prematurely up taking water and adhering to itself and said hydrophilic surfactant acts as a carrier for said hydrophobic silicone compound upon entrance into an aqueous environment.

19. The medical device of claim 18 wherein said device is a dilatation balloon.

20. The medical device of claim 18 wherein said hydrophilic coating is a polymeric material selected from the group consisting of polyalkylene glycols, alkoxy polyalkylene glycols, copolymers of methylvinyl ether and maleic acid, poly(vinylpyrrolidone), poly(N-alkylacrylamide), poly (acrylic acid), poly(vinyl alcohol), poly(ethyleneimine), polyamides, methyl cellulose, carboxymethyl cellulose, polyvinyl sulfonic acid, heparin, dextran, modified dextran and chondroitin sulphate.

21. The medical device of claim 20 wherein said hydrophilic coating comprises at least one polymer selected from the group consisting of copolymers of maleic anhydride and polycarboxylic acids.

22. The medical device of claim 18 wherein said hydrophobic silicone compound is a siloxane.

23. The medical device of claim 18 wherein said hydrophilic surfactant is selected form the group consisting of polyalkylene glycols, alkoxy polyalkylene glycols, ethoxylated castor oil, and mixtures thereof.

24. A medical device adapted for insertion into the body of a patient and manipulation from outside of the body, comprising an elongate body for insertion into said body wherein said elongate body is coated with a first hydrogel polymeric layer and a second hydrophobic coating wherein said hydrophobic comprises at least one hydrophilic surfactant.

\* \* \* \* \*